US009820718B2

United States Patent
Flomerfelt et al.

(10) Patent No.: US 9,820,718 B2
(45) Date of Patent: Nov. 21, 2017

(54) ENHANCED ELECTRONIC EXTERNAL FETAL MONITORING SYSTEM

(71) Applicant: Syracuse University, Syracuse, NY (US)

(72) Inventors: Kimberly Flomerfelt, Manlius, NY (US); Patrick Mather, Manlius, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 13/782,559

(22) Filed: Mar. 1, 2013

(65) Prior Publication Data

US 2013/0281861 A1 Oct. 24, 2013

Related U.S. Application Data

(60) Provisional application No. 61/605,519, filed on Mar. 1, 2012.

(51) Int. Cl.
| | |
|---|---|
| *A61B 8/00* | (2006.01) |
| *A61B 8/08* | (2006.01) |
| *A61B 8/02* | (2006.01) |
| *A61B 5/00* | (2006.01) |
| *A61B 5/024* | (2006.01) |

(Continued)

(52) U.S. Cl.
CPC .......... *A61B 8/0866* (2013.01); *A61B 5/0011* (2013.01); *A61B 5/0205* (2013.01); *A61B 5/02411* (2013.01); *A61B 5/4356* (2013.01); *A61B 5/4362* (2013.01); *A61B 8/02* (2013.01);
(Continued)

(58) Field of Classification Search
CPC ....... A61B 8/02; A61B 5/0205; A61B 5/4356; A61B 5/02411; A61B 5/0011
See application file for complete search history.

(56) References Cited

U.S. PATENT DOCUMENTS 3,721,988 A * 3/1973 Schwartz ............. H01Q 25/004
343/756
3,943,918 A 3/1976 Lewis
(Continued)

FOREIGN PATENT DOCUMENTS

| EP | 0345471 | 12/1989 |
|---|---|---|
| WO | 2005110236 | 11/2005 |

(Continued)

OTHER PUBLICATIONS

Octavio de Oliveira Santos Filho et al. "Repurcussions of previous cesarean uterine scar at uterine arteries Doppler velocimetry between the 26$^{th}$ and 32$^{nd}$ gestational weeks." Radiol Bras. 2011 44(3):163-166.*

(Continued)

*Primary Examiner* — Amanda Lauritzen Moher
(74) *Attorney, Agent, or Firm* — Bond Schoeneck & King, PLLC; George McGuire; Frederick Price (57) ABSTRACT

The present invention relates to fetal monitoring and, more particularly, to an electronic external fetal monitoring system that includes a self adhering single use dermal patch including embedded sensors that can be attached to the skin of an expectant maternal patient and is configured to record fetal heart rate, uterine activity, and uterine integrity.

12 Claims, 10 Drawing Sheets

(51) Int. Cl.
  *A61B 5/0205*   (2006.01)
  *A61B 8/06*     (2006.01)

(52) U.S. Cl.
  CPC .............. *A61B 8/06* (2013.01); *A61B 8/4236* (2013.01); *A61B 8/488* (2013.01); *A61B 8/4281* (2013.01)

(56) References Cited

U.S. PATENT DOCUMENTS

| | | | |
|---|---|---|---|
| 3,989,034 A | | 11/1976 | Hojaiban |
| 5,042,503 A | | 8/1991 | Torok |
| 5,224,490 A | | 7/1993 | Allen et al. |
| 5,265,613 A | | 11/1993 | Feldman |
| 5,377,673 A | | 1/1995 | Van Dell |
| 5,431,171 A | | 7/1995 | Harrison |
| 5,807,271 A | | 9/1998 | Tayebi |
| 5,829,438 A | * | 11/1998 | Gibbs et al. ................. 600/588 |
| 5,865,733 A | | 2/1999 | Malinouskas |
| 5,882,300 A | | 3/1999 | Malinouskas |
| 5,882,305 A | | 3/1999 | Dumoulin |
| 5,899,861 A | | 5/1999 | Friemel |
| 5,919,141 A | | 7/1999 | Money |
| 5,935,061 A | * | 8/1999 | Acker et al. ................. 600/304 |
| 6,115,624 A | | 9/2000 | Lewis |
| 6,171,263 B1 | | 1/2001 | Sullivan |
| 6,440,089 B1 | | 8/2002 | Shine |
| 6,454,716 B1 | | 9/2002 | Zumeris |
| 6,497,661 B1 | | 12/2002 | Brock-Fisher |
| 6,579,231 B1 | | 6/2003 | Phipps |
| 6,658,284 B1 | | 12/2003 | Rosen |
| 6,751,498 B1 | * | 6/2004 | Greenberg ......... A61B 5/02405 600/511 |
| 6,798,199 B2 | | 9/2004 | Larson |
| 7,382,247 B2 | | 6/2008 | Welch |
| 7,470,232 B2 | * | 12/2008 | Hoctor et al. ................. 600/453 |
| 7,519,417 B2 | | 4/2009 | Ferguson |
| 7,532,923 B1 | | 5/2009 | Hayes-Gill |
| 7,539,534 B2 | | 5/2009 | Orenstein |
| 7,593,765 B2 | | 9/2009 | Rapoport |
| 7,783,095 B2 | | 8/2010 | Carneiro |
| 7,789,836 B2 | * | 9/2010 | Van Wyk et al. ............ 600/459 |
| 7,818,050 B2 | | 10/2010 | Rapoport |
| 7,831,302 B2 | | 11/2010 | Thomas |
| 7,850,625 B2 | * | 12/2010 | Paltieli et al. ................. 600/588 |
| 7,854,237 B2 | * | 12/2010 | Irland .......................... 137/223 |
| 7,976,480 B2 | | 7/2011 | Grajales |
| 8,043,233 B2 | * | 10/2011 | Paltieli et al. ................. 600/588 |
| 8,116,847 B2 | | 2/2012 | Gattani |
| 8,150,502 B2 | | 4/2012 | Kumar |
| 8,160,692 B2 | | 4/2012 | Principe |
| 8,214,007 B2 | | 7/2012 | Baker |
| 8,229,550 B2 | | 7/2012 | James |
| 8,244,335 B2 | | 8/2012 | Kumar |
| 2003/0191392 A1 | * | 10/2003 | Haldeman ................. A61B 8/12 600/467 |
| 2005/0251044 A1 | * | 11/2005 | Hoctor et al. ................. 600/444 |
| 2006/0047215 A1 | | 3/2006 | Newman |
| 2007/0167753 A1 | * | 7/2007 | Van Wyk et al. ............ 600/437 |
| 2007/0191728 A1 | * | 8/2007 | Shennib ...................... 600/546 |
| 2007/0255184 A1 | | 11/2007 | Shennib |
| 2007/9255184 | | 11/2007 | Shennib |
| 2008/0125652 A1 | | 5/2008 | Clark |
| 2008/0167553 A1 | * | 7/2008 | Paltieli et al. ................. 600/437 |
| 2009/0143650 A1 | | 6/2009 | Guion-Johnson et al. |
| 2009/0216564 A1 | | 8/2009 | Rosenfeld |
| 2010/0168528 A1 | | 7/2010 | Evans et al. |
| 2010/0168596 A1 | | 7/2010 | Jaeschke |
| 2010/0235782 A1 | | 9/2010 | Powell |
| 2010/0305481 A1 | | 12/2010 | Igney |
| 2012/0150010 A1 | | 6/2012 | Hayes-Gill |

FOREIGN PATENT DOCUMENTS

| | | |
|---|---|---|
| WO | 2007095455 | 8/2007 |
| WO | 2008073491 | 6/2008 |
| WO | 2010124117 | 10/2010 |
| WO | 2011023521 | 3/2011 |

OTHER PUBLICATIONS

PeriCALM Shoulder Screen, www.perigen.com, Oct. 11, 2013.
PeriCALM, www.perigen.com, Oct. 11, 2013.
PeriBIRTH, www.perigen.com, Oct. 11, 2013.
International Search Report Form PCT/ISA/210, International Application No. PCT/US2013/028628, pp. 1-11, dated Jun. 24, 2013.
International Search Report EPO Form 1507S, International Application No. PCT/US2013/028628, p. 1-6, dated Sep. 9, 2015.
Examination Search Report for Canadian Patent Application No. 2,866,089 (PCT/US2013/028628, pp. 1-7, dated Nov. 24, 2015.

* cited by examiner

ENHANCED ELECTRONIC EXTERNAL FETAL MONITORING SYSTEM

The present application claims benefit of U.S. provisional patent application No. 61/605,519, filed Mar. 1, 2012, and is hereby incorporated by reference in its entirety.

BACKGROUND OF THE INVENTION

1. Field of the Invention

The present invention relates to fetal monitoring and, more particularly, to an electronic external fetal monitoring system that includes a self adhering single use dermal patch including embedded sensors that can be attached to the skin of an expectant maternal patient and is configured to record fetal heart rate, uterine activity, and uterine integrity.

2. Description of the Related Art

Accurately evaluating the well-being of a fetus during labor and delivery is tantamount in providing a plan of care that will ensure the most desired outcome (i.e., healthy newborn and mother). Electronic Fetal Monitoring technology/devices, EFM, was developed in the 1960's, and became routinely used in hospitals by the late 1970's. EFM is used to evaluate fetal well-being during the labor process by recording fetal heartbeat and frequency of uterine contractions via two monitors—an ultrasound device (US) and tocodynameter (TOCO), respectively.

Today EFM is the most common obstetrical procedure in the US, estimated at 8 million applications annually. Virtually every woman undergoes EFM during pregnancy, and labor and delivery. EFM has also become the standard of care in obstetrical settings worldwide.

In brief, during labor, care providers perform a Leopold Maneuver on the gravid abdomen to try to detect the lie of the fetus in the uterus. Placing the US over the fetal back, once detected, is usually the best location to record consistent fetal heart beat. Ultrasonic gel must be applied between the US device and the skin surface to function properly. The US is held to the abdomen with an elastic belt. The TOCO is applied to the abdomen above the umbilicus where the fundal height of the uterus is palpated, and is held to the upper part of the abdomen by an elastic belt.

EFM technology has not changed much since its inception, although care providers are relying more heavily on the data this technology provides and some improvements have been made in the interpretation of this data. It is therefore very important to record the most consistent, accurate, and reliable data possible. Physicians are under tremendous pressure from lawsuits to intervene when any indication elicited from the EFM technology alerts the physician to a change in fetal well-being during labor. Whenever there is inconsistent data from the EFM technology, care providers often have to choose the plan of care with the least amount of risk to the fetus. In many cases this means cesarean birth.

Current interpretation of data gathered by conventional EFM technology involves subjective interpretation of the data by the clinician, i.e., the clinician uses his/her trained eye to monitor a strip of data indicating fetal heart rate and uterine contractions over a specific period of time (as should be understood by those skilled in the art).

The first thing a clinician determines when interpreting EFM data is the baseline fetal heart rate. The baseline is defined as the average heartbeat between contractions, consistent for 10 or more minutes; for example, 140 bpm (beats per minute). The next step is to determine variability. Variability is the variance in the baseline, also described in beats per minute, bpm. There are four categories of variability: Absent: none detected; minimal: 1-5 bpm; moderate: 6-25 bpm; and marked: >25 bpm. Moderate variability indicates fetal well-being, while absent, minimal, or marked variability can indicate fetal distress.

The next step is to determine the presence or not of accelerations in the fetal heart rate. For neonates, accelerations are defined as an increase in fetal heartbeat by 15 bpm over baseline for a duration of 15 seconds. As an example clinical assessment, the clinician may note fetal heartbeat 140 bpm, moderate variability, with accelerations noted.

Finally, the clinician determines the presence and nature of decelerations. There are four categories of decelerations. (i) Early deceleration is a decrease in the fetal heart beat 15 bpm under baseline for the peak of the contraction. Early decelerations return to baseline as the contraction ends. Early decelerations are benign, and usually indicate head compression. (ii) Variable deceleration, can be abrupt decreases in baseline up to 25 bpm below baseline, usually at the peak of a contraction. Variable decelerations return to baseline at the end of the contraction. Variable decelerations usually indicate umbilical cord compression. Variable decelerations require close monitoring, as they can be benign, or become indication of fetal distress. (ii) Late decelerations are defined as a gradual decrease in fetal heart beat of 1-15 bpm below baseline, which occur after the nadir of a uterine contraction, and return to baseline after the contraction is completed. Late decelerations usually indicate placental insufficiency, and indicate fetal distress. Delivery should be imminent when a repetitive pattern of late decelerations is noted, especially if variability is also minimal. (iii) Prolonged decelerations are defined as deceleration 1-25 bpm below baseline for 2 or more minutes. Prolonged decelerations are indicators of fetal distress, and fetal hypoxia may be suspected.

EFM also records uterine activity. Interpretation of uterine activity in EFM includes the frequency and duration of contractions. Frequency is determined by counting the minutes between the start of one contraction, to the start of the next contraction. Duration is the time (generally indicated in seconds) between the beginning and end of a contraction. For example, uterine contractions can be every 3 minutes, lasting 60 seconds. External monitoring cannot measure strength of contractions quantitatively. Absent a quantitative measure, clinicians judge the strength of contractions by palpating the fundus during a contraction, observing the patients response to the contraction, and considering the progression of cervical change.

Description of the Related Art Section Disclaimer: To the extent that specific patents/publications are discussed above in this Description of the Related Art Section or elsewhere in this Application, these discussions should not be taken as an admission that the discussed patents/publications are prior art for patent law purposes. For example, some or all of the discussed patents/publications may not be sufficiently early in time, may not reflect subject matter developed early enough in time and/or may not be sufficiently enabling so as to amount to prior art for patent law purposes. To the extent that specific patents/publications are discussed above in this Description of the Related Art Section and/or throughout the application, they are all hereby incorporated by reference into this document in their respective entirety(ies).

SUMMARY OF THE INVENTION

The present invention recognizes that there are potential problems and/or disadvantages in the conventional EFM technology. For example, the main problems of conventional EFM technology include (i) inconsistent data acquisition; (ii) patient discomfort; (iii) lack of automatic data synthesis and interpretation; and (iv) hygienic concerns.

Inconsistent data acquisition occurs because current EFM technology does not record data consistently when the fetus, mother, or monitor moves. Without consistent data acquisition, care providers are unsure if the fetus is at risk for complications resulting from intolerance of labor. Data gathered from the use of EFM and interpretation of this data is the best tool care providers have to determine fetal well-being; however, it is only valuable if it is consistent data. Care providers must be able to witness consistent fetal heart rate patterns and responses of fetal heart rate to uterine contractions to determine if the plan of care is the most prudent medical care. Additionally, uterine contractions can be difficult to record when the mother has copious abdominal fat, since the TOCO operates by sensing the hardening of the uterus during a contraction. When a care provider does not have consistent data relating to fetal well-being during labor, often times the most prudent action is to opt for a cesarean birth. Cesarean birth rates have risen in recent years, in part because of questionable fetal well-being, which is directly related to inconsistent monitoring. Cesarean births can cost hospitals, insurance companies, and physicians more money than vaginal births when argument is initiated on whether a cesarean birth was indeed necessary.

As with any surgical scar, tissue that has been incised has potential to lose its integrity under strain. After a woman has a cesarean birth, she is advised to have all future births via cesarean method. This is because there is no monitoring available to gather consistent reliable data to allow a clinician to determine if the uterine scar from the previous cesarean will remain intact during labor until it is too late (i.e., an obstetric emergency with risk to fetal and maternal life). Today, most obstetricians do not offer trial of labor for vaginal birth, after cesarean birth for this reason. This has not always been the case, and there are many women who are good candidates to attempt vaginal birth after cesarean.

EFM is a challenge in obese patients, as noted above. Conventional EFM technology/devices do not provide consistent data in obese patients. In order to get the best fetal heart rate signal, a nurse has to palpate the fetus in the woman's uterus to determine fetal lie, enabling placement of the EFM device over the fetal back. Often this is not possible, and the nurse has to place the EFM device in one quadrant at a time to search for the fetal heartbeat. The ultrasound in the conventional EFM device is approximately 2.5 inches in diameter, and ultrasonic gel is applied. Currently, EFM devices record presence of uterine contractions by use of a pressure sensitive disc. This is the tocodynamometer. When placed over the fundus, distal end of the uterus, during a contraction the fundus presses the disc. The pressure is translated into a bell curve on the EFM record. In obese patients, there is often difficulty in recording contractions because the fundus cannot be palpated through thick layers of adipose tissue.

Every time there is inconsistent data or loss of recording of contractions or fetal heart rate, which frequently occurs, a care provider must readjust the monitor placement. This is often a repetitive disruption for the laboring patient causing patient anxiety and patient discomfort. Also, as discussed above, current EFM monitoring is done with two separate bulky plastic reusable transducers held to the abdomen with elastic belts. These transducers move constantly, thus interrupting the recording of fetal heart beat and contraction frequency. The transducers move because they are not adhered to the skin. When a patient changes position in bed, to sit up for a drink of water, or lay on her side, the belts may loosen or tighten, and the transducer moves. Patients report discomfort related to belts being too tight, feeling like they can't move freely, and feeling wet from the ultrasound gel. Patients also complain that frequent readjustments are necessary to record fetal heart beat and contraction pattern. Each time the monitors require adjustment the patient's gown is lifted to expose the abdomen. Care is taken to protect patients privacy, and ensure modesty, however many patients verbalize being uncomfortable being exposed frequently in front of their labor coaches. A patient currently must ring a call bell for the nurse to come unhook the monitors if she needs to use the restroom. Waiting for a nurse to come to the room can be a source of frustration for the patient, as their autonomy is damaged. They cannot carry out the simple task of going to the bathroom by themselves because of the monitor. Some women may experience embarrassing bowel occurrences in labor, such as diarrhea or constipation, and having to ask for 'permission' to use the restroom is often a source of discomfort. The patient discomfort is also related to ultrasonic gel often being applied all over the abdomen to record the fetal heart rate.

Further, without automatic data synthesis—particularly of contraction and fetal heart rate data sets—unnecessary subjectivity for healthcare decision-making results. "Eye-balling" a chart of contraction vs. time and fetal heart rate versus time to lead to a conclusion concerning baby health is archaic.

Moreover, since current EFM devices are reusable, they can be sources of infectious blood and other bodily fluids creating a potentially hazardous hygienic problem.

Various embodiments of the present invention may be advantageous in that they may solve or reduce one or more of the potential problems and/or disadvantages discussed above in this Summary of the Invention section.

It is therefore a principal object and advantage of the present invention to provide an electronic external fetal monitoring system that can provide clinicians with more consistent and accurate data (as compared with conventional EFM technology) to enable clinical decisions to be made more effectively and efficiently and to ensure fetal and maternal well-being during labor, thereby decreasing fetal and maternal mortality rates.

It is a further object and advantage of the present invention to provide an electronic external fetal monitoring system that can provide greater patient comfort, allow more freedom of patient movement during labor and delivery, decrease patient anxiety, and provide improved hygiene over conventional EFM technology.

It is a further object and advantage of the present invention to provide an electronic external fetal monitoring system that can provide physicians accurate, consistent, reliable data to form a well-reasoned and effective plan of care.

It is an additional object and advantage of the present invention to provide an electronic external fetal monitoring system including enhanced signal stability compared with conventional EFM devices, and one time application without the need for ultrasonic gel.

It is a further object and advantage of the present invention to provide an electronic external fetal monitoring system that can provide a new standard of monitoring that would support clinical decisions made by labor and delivery personnel.

It is an additional object and advantage of the present invention to provide an electronic external fetal monitoring system that can standardize protocols for clinical decisions in vaginal births, and thus improve outcomes in vaginal births.

In accordance with the foregoing objects and advantages and as described further in the Detailed Description Section herein, an embodiment of the present invention relates to an electronic external fetal monitoring system that includes a single use use/disposable self adhering dermal pad or patch containing sensors configured to allow the detecting/gathering/recording of uterine contractions (e.g., through application of a strain gauge), uterine integrity (at the area of a previous cesarean section scar on uterus) and fetal heartbeat (e.g., through polymeric ultrasonic transduction), without the use of belts. An embodiment of the present invention contemplates an electronic external fetal monitoring system that can also monitor the mother's heartbeat. Similar to electrode pads used for an EKG, an embodiment of the present invention contemplates a TOCO that is re-designed to sense uterine contractions by resistive changes to the strain-gauge. This can improve consistency in recording uterine contractions, particularly in overweight patients.

An ultrasonic Doppler Flow imaging sensor (which is configured to be small enough to fit in the strip discussed further below) can be implemented as part of an electronic external fetal monitoring system of an embodiment of the present invention to monitor uterine integrity, which is especially important where trial of labor is indicated for an attempt at VBAC (vaginal birth after cesarean). The ultrasound is capable of showing motion, and muscle contraction, color flow Doppler of blood flow, and tissue spectral analysis. This technology can give physicians a tool to maintain patient safety during VBAC.

It is contemplated that in a preferred embodiment, the self adhering patch of an electronic external fetal monitoring system will appear as a single disposable soft piece of foam the thickness of about two quarters that comfortably adheres to the lower aspect of the abdomen. The patch will have impregnated sensors within a gel layer that would record fetal heart rate, and uterine muscle activity, and uterine integrity. The fetal heart rate can be measured by interpretation of signal acquired from the pitch catch (sometimes called pulse-receive) ultrasound technique. Alternatively, in the way in which an echocardiogram visualizes the beating heart, fetal heart beat could be detected by having real time ultrasound embedded in the patch. Fetal position for vaginal birth is cephalic vertex, or head first. Therefore, it is envisioned that such a sensor over the lower abdomen would capture signal from fetal carotid pulse, or heartbeat. Uterine activity can be monitored by the same real time ultrasound. Just as in and echocardiogram, the muscles of the heart can be visualized as moving during contraction, uterine contractions could also be viewed. Ultrasonic Doppler flow imaging technology already existing, could be employed to monitor the flow of blood within the uterine wall. In an echocardiogram, blood can be watched as red or blue matter flowing between the valves of the heart. In cases of dysfunctional valves, the red and blue blood mix, and the diagnosis is apparent. Detecting blood flow from outside the uterine wall would tell clinicians the uterus may rupture, and immediate surgical birth intervention can make the difference between a live, and still born infant.

As an electronic external fetal monitoring system of an embodiment of the present invention can utilize piezoelectric thin film polymeric ultrasonic transducers, acoustic coupling gel may be needed and should be contained in the device. Additionally, gel can be required for those functions of the electronic external fetal monitoring system of an embodiment of the present invention involving the sending and/or receiving of acoustic signals, which include heart rate monitoring (fetal and maternal) and "pulse-echo" measurement of the contractions for obese patients. For other patients, contraction strength can be measured by sensor flexure (resistive changes (of strain gauges)), which does not require application of ultrasonic gel. Further, the gel can be included at the interface between sensor and patient in much the same fashion as EKG and EEG electrodes. Thus, a disposable, paper-based ply can be removed prior to use, exposing both gel and adhesive for the application. These modifications can greatly improve data recording, patient comfort and hygiene.

In accordance with an embodiment of the present invention, PVDF sensors are embedded into the patch. The sensors are configured in multiple modes (e.g., 2 modes): one mode for detecting fetal heart and maternal heart beats, and the other mode to detect uterine activity utilizing pitch catch method. Signal processing will sort the fetal and maternal heart rates. The algorithm described herein will work with this patch to analyze the data. This embodiment can also have maternal pulse oximetry capabilities, and non invasive fetal pH monitors.

In accordance with an embodiment of the present invention, a uterine integrity monitor is contemplated, which can include a self adhering gel layered patch with color flow doppler/spectroscopy technology sensor (ultrasonic Doppler flow imaging technology) to monitor uterine integrity at the site of a previous cesarean birth scar. It can be configured to provide real time monitor/observation of the uterine scar during labor to look for leakage of blood or amniotic fluid from the scar during contractions. In the case of evidence of fluid leaking from the uterine scar, or any indication of scar separation during labor, a clinician can intervene accordingly with more reaction time than without the monitor.

In accordance with an embodiment of the present invention, a combination patch, combining the patches described in the two previous paragraphs is contemplated.

In accordance with an embodiment of the present invention, use of a rechargable battery for the patch is contemplated. A hydrogen peroxide sterilization procedure, used increasingly in hospitals, can be employed to disinfect/sterilize the cell phone sized, for example, battery pack the patient can wear while she is being monitored. The patch can have a metal coil around its perimeter that will power the unit in concert with the battery pack.

In accordance with an embodiment of the present invention, data transmission can occur pursuant to blue tooth technology. For example, a network device can sit at the nurse's station, or patients room creating a zig-bee mesh through which the data can be transmitted to MD/clinicians secured iphone devices. Care can be taken to ensure HIPPA specifications will be met. In a rural setting, where patients are 50-100+ miles from care facilities, clients could attach the device to the abdomen, and the data could be viewable by MD/clinician from his/her alternate remote location.

In accordance with an embodiment of the present invention, a data synthesis algorithm is provided that can be used to assist with an objective interpretation or synthesis of data generated (e.g., related to fetal heart rate and uterine contractions) by conventional EFM technology and/or by an electronic external fetal monitoring system of an embodiment of the present invention. The data can be quantitatively analyzed with algorithms to interpret the data within the direction of the American College of Obstetricians and Gynecologists, ACOG. In a preferred embodiment, the algorithm can be programmed into firmware (as should be appreciated and understood by those skilled in the art), or in a software program running on a computer receiving the data, and displayed in real time on a graph, as well as the quantitative analysis.

In accordance with an embodiment of the present invention, a method of using an electronic external fetal monitoring system of an embodiment of the present invention is also provided.

BRIEF DESCRIPTION OF THE DRAWINGS

The present invention will be more fully understood and appreciated by reading the following Detailed Description in conjunction with the accompanying drawings, in which:

FIG. 5 shows (a) a schematic representation of the major fetal heart rate responses to a contraction, and (b) a graphical representation of the parameterization of the position, magnitude, and shape/width of fetal heart rate responses to a contraction in accordance with an embodiment of the present invention.

DETAILED DESCRIPTION

The present invention will be more fully understood and appreciated by reading the following Detailed Description in conjunction with the accompanying drawings, wherein like reference numerals refer to like components.

Figure 1:
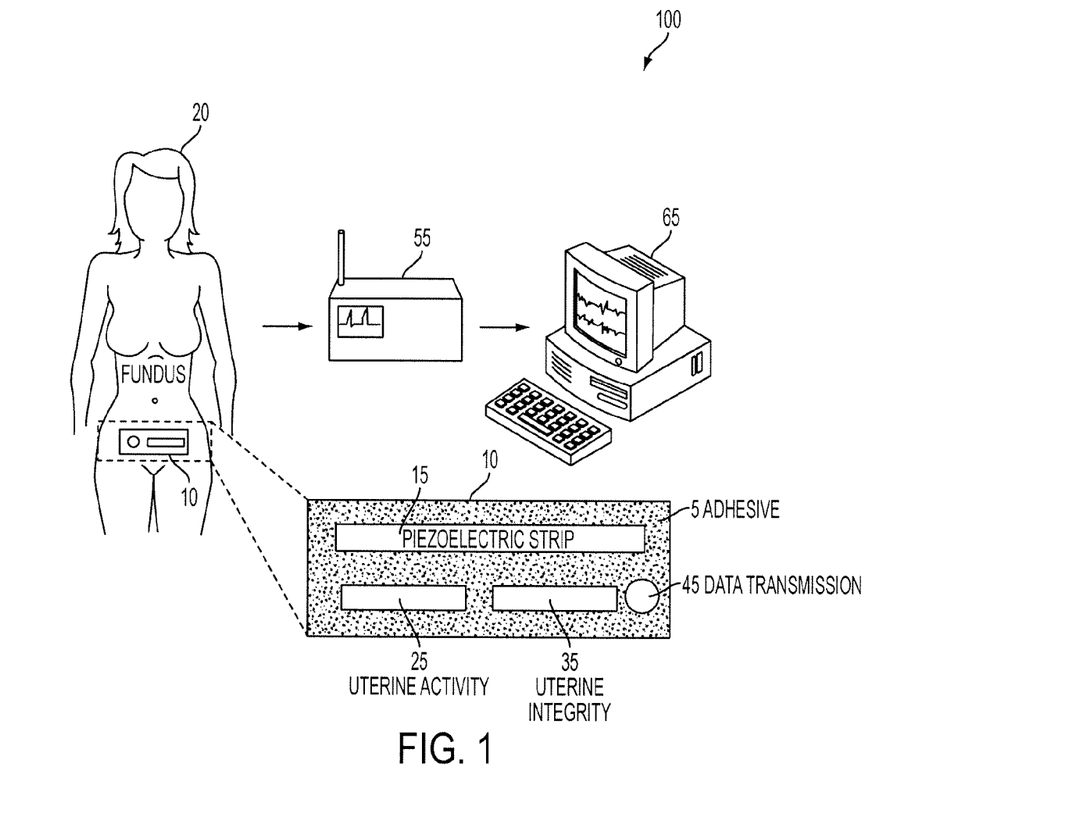
FIG. 1 is a schematic representation of an electronic external fetal monitoring system in accordance with an embodiment of the present invention.

Turning to FIG. 1, a perspective view of an electronic external fetal monitoring system 100 is shown in accordance with an embodiment of the present invention. The electronic external fetal monitoring system 100 includes a preferably single use, disposable, self adhering dermal patch 10 which includes one or more of the following: an adhesive material 5 for attaching the patch 10 to the skin of the patient, a portion 15 for collecting and recording data related to fetal heart rate and/or the heart rate of the expectant mother, a portion 25 for collecting and recording data related to uterine activity, a portion 35 for collecting and recording data related to uterine integrity, and a portion 45 for data transmission purposes (i.e., a portion configured to transmit data related to fetal/expectant mother heat rate, uterine activity, and/or uterine integrity to a monitor device 55 and/or a computer 65 with a display screen (e.g., laptop, desktop, smart phone, cell phone, computer tablet, and/or other portable computer like device) and running a computer program for further analysis. FIG. 1 also shows the self adhering dermal patch 10 attached to the skin of the expectant mother patient 20 toward the lower part of the abdomen. The patch can also contain a battery or batteries, not shown.

In a preferred embodiment, a piezoelectric polymer strip can be used at portion 15 to record fetal heartbeat. This can enable consistent recording regardless of patient, fetal movement, and would eliminate monitor movement. Piezoelectric polymer strip incorporation would allow for a broader sensing of heartbeat, and can be smaller than current ultrasound devices use for hand-held imaging. Uterine activity can be recorded using a pressure disc, a strain gauge, or physiologic change sensors at portion 25. Uterine integrity can be further monitored via real time ultrasound at portion 35, with an additional monitor applied to the patient undergoing a trial of labor after cesarean delivery. The real time ultrasound can be employed on the lower transverse section of the abdomen to visualize uterine integrity during trial of labor. This particular uterine activity monitoring can be utilized in the case of a premature labor patient with a previous cesarean to determine her plan of care (i.e.; tocolysis versus delivery). Use of the real time ultrasound monitor could also be used in patients at risk for premature separation of the placenta from the uterine wall, known as abruption, which is also an obstetric emergency.

In accordance with an embodiment of the present invention, a single ultrasonic strip can be used to record data relating to two or more of the following: maternal heart rate, fetal heart rate, uterine activity, and/or uterine integrity (e.g., a thin film poly(vinylidene fluoride) (PVDF) strip at portion 15 only; PVDF is a preferred embodiment of the piezoelectric polymer strip/film). This single strip monitoring can be accomplished through the use of modes of data gathering that can be controlled at a point away from the dermal patch 10, e.g., at the monitor 55 or the computer 65. That is, the computer can have a mechanism that allows the user to select/change data gathering/recording mode depending upon which type of data is sought to be monitored (e.g., mode 1=maternal hear rate; mode 2=fetal heart rate; mode 3=uterine activity; and mode 4=uterine integrity).

In a preferred embodiment, the patch 10 is about ¼ inches or smaller in profile, 2-4 inches in width, and about 4-8 inches in length. The patch 10 can transmit the data it gathers/records through a wire attached to a monitor 55/computer 65 or the patch 10 can transmit this data wirelessly. The wireless transmission can be accomplished through any wireless protocol/technology, including, but not limited to, ZigBee standards-based protocol, Bluetooth technology, and/or Wi-Fi technology. The monitor and computer can be located in the same room, in a different room in the same building, and/or in a completely different building and location from the patient wearing the patch 10.

Figure 2:
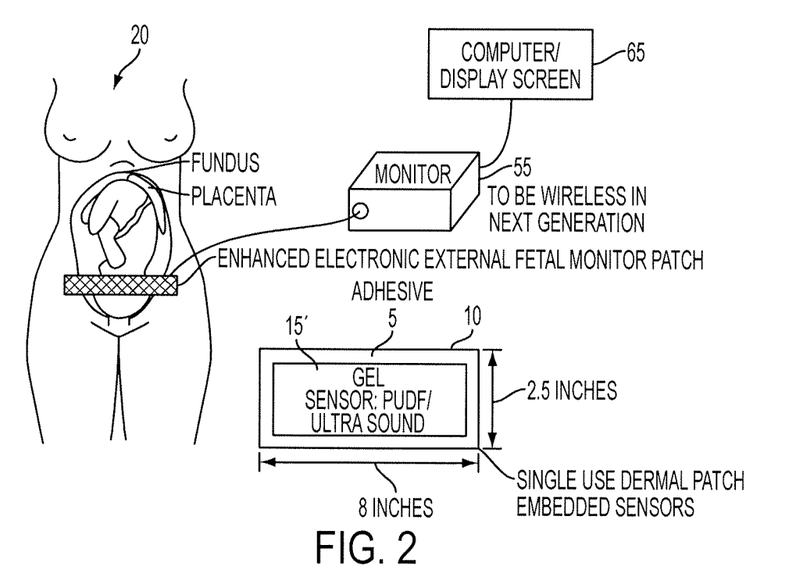
FIG. 2 is a schematic representation of an electronic external fetal monitoring system in accordance with an embodiment of the present invention.

Turning to FIG. 2, another illustration of the self adhering single use dermal patch 10 including embedded sensors attached to the skin of an expectant maternal patient 20 toward the lower part of the abdomen is shown. The patch 10 is shown with an adhesive (e.g., Hypafix tape, other medical tape or glue like adhesive material). A sensor portion 15' is also shown (which can be a single portion or multiple portions) and can include sensors such as a PVDF contact microphone, and/or a piezoelectric ultrasonic transducer. Gel can be applied to the sensor portion(s). A monitor 55 and a computer/display screen 65 are also shown.

The principles of use of an electronic external fetal monitoring system of an embodiment of the present invention include utilizing microphone and pitch-catch methods of ultrasonic sensing to detect heart beat and to measure uterine activity/contractions. Pressure discs, strain gage, and/or physiologic change sensors can be used to fine tune data collection.

In accordance with an embodiment of the present invention, an electronic external fetal monitoring system is constructed and used in a particular manner that can be especially helpful in obese patients. For example, an electronic external fetal monitoring system is provided that employs a broader, more sensitive ultrasound capability that would pick up fetal heart beat, without necessarily being directly over the fetal back. In addition, the electronic external fetal monitoring system can record uterine activity at the low transverse section of the abdomen, at the distal end of the uterus. Rather than employ pressure sensitive disc, uterine contractions can be recorded with ultrasound (as described above). This can be accomplished by real time ultrasound, translating muscle movement into a bell curve, or measurement of other physiologic changes.

Figure 3:
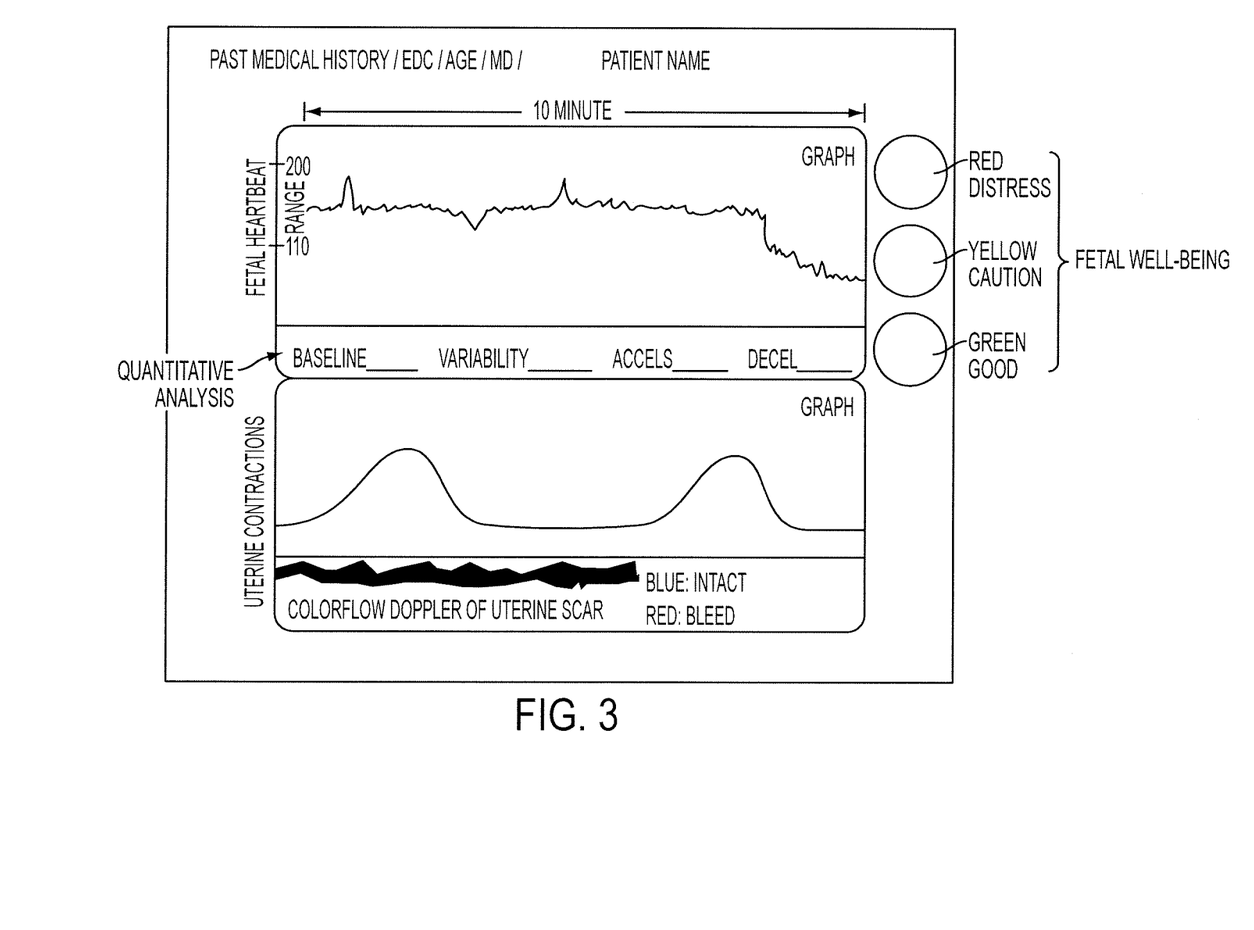
FIG. 3 is a graphical representation of a user interface used in conjunction with the enhanced electronic fetal monitoring system of an embodiment of the present invention.

FIG. 3 shows a user interface used in conjunction with the enhanced electronic fetal monitoring system of an embodiment of the present invention. The top graph displays a time series of acquired fetal heart rate data while the bottom graph displays the contraction magnitude, each continuously sweeping with the passage of time. Additional features shown are the ultrasonic Doppler flow imaging assessment of uterine scar health (bottom) and algorithm-based assessment of fetal health in color form (upper right).

In accordance with an embodiment of the present invention, real time quantitative analysis of fetal heart rate and uterine contraction data is contemplated in order to eliminate subjective interpretation of this data. It is critical to have a recording of the fetal heart beat and the precise beginning and end of a contraction to determine fetal well-being, and an electronic external fetal monitoring system of an embodiment of the present invention can deliver a far superior recording than existing EFM. Furthermore and as further described below, objective data synthesis is possible. A data synthesis algorithm has been developed by combining contraction and fetal heart rate signals into useful knowledge that can guide clinicians in objectifying otherwise subjective data syntheses as described above.

Event Parameterization.

Figure 4:
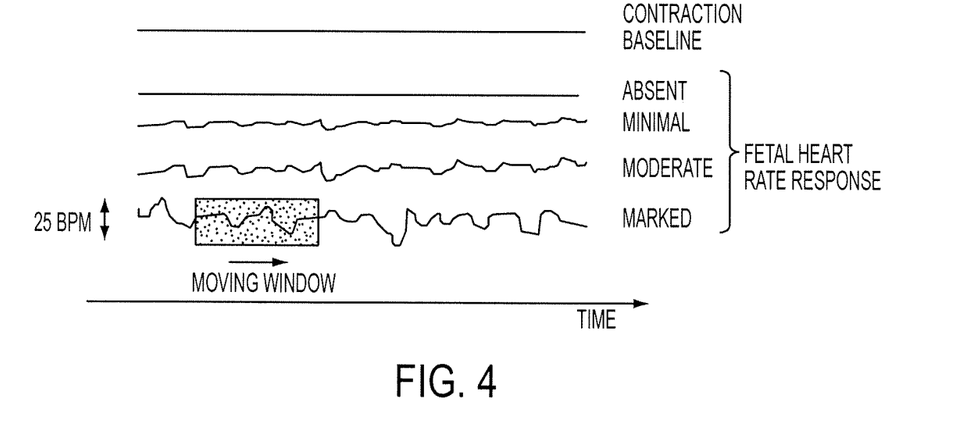
FIG. 4 is a schematic representation of a moving window of a particular time frame over a particular fetal heart rate response (including absent, minimal, moderate, and marked) to a particular uterine contraction, in accordance with an embodiment of the present invention.

Critical to the algorithm for objective assessment of an embodiment of the present invention is first parameterizing both the fetal heart rate signal and the uterine contraction signal, each obtained from the patch 10 of an electronic external fetal monitoring system 100 (as described above, for example). To begin, the variability in fetal heart rate signal, shown at the different possible levels of variability, will be quantified using the standard deviation formula with a moving window (shown in FIG. 4) of 60 seconds, for example. FIG. 4 shows a range of time-series graphs of the fetal heart rate signal during the period of time absent any contraction. Indicated to the right of each trace are descriptions commonly used in practice to describe the different levels of heart rate variability, including "absent" (no variability whatsoever), "minimal" (slight variability detected), "moderate" (moderate variability detected), and "marked" (significant variability detected). These are subjective classifications. Needed are objective measurements, which this invention, in part, addresses. The "moving window" shown indicates the time domain used for objective quantification of fetal heart rate variability. Other time frames may be used for the moving window as deemed appropriate by the clinician.

In particular, the variability measure will be:

$$VAR = \left(1/N \sum_{i=1}^{N} (y_i - y_{ave})^2\right)^{1/2},$$

where $y_i$ is the fetal heart rate measurement, $y_{ave}$ is the average fetal heart rate in the sampling window, and N is the number of data in the window. This quantity will have units of bpm and is a commonly accepted measure of variability for use in statistical analyses.

Figure 5A:
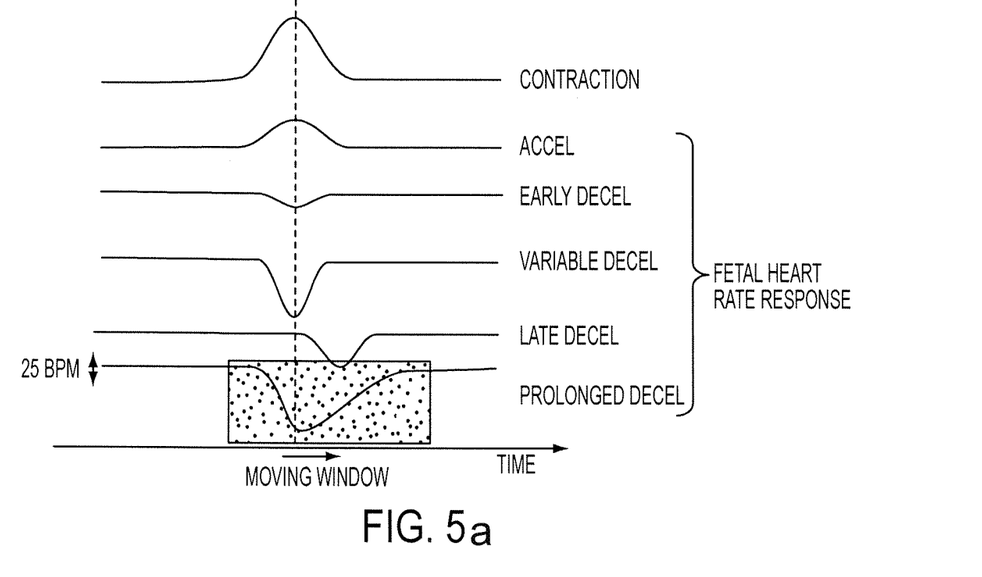

As described above, beyond baseline regions of no contraction activity, the fetal heart rate responses are very telling indicators of fetal health. Thus, combined analysis of fetal heart rate and uterine contraction activity is necessary. Importantly, contractions and fetal heart rate responses alike can be described mathematically by either Gaussian or log-normal functions provided that the parameters of each are adjusted to best fit the acquired data. Such fitting can be done "on the fly" with embedded computing to yield the function parameters. Further, parameters of these fits can be combined (or compared) in an algorithm to measure fetal health. FIG. 5a shows a schematic representation of the major fetal heart rate responses to a contraction, in accordance with an embodiment of the present invention.

As illustrated in FIG. 5a, a heart rate response characteristic or characteristics is shown associated with direction (accel/up or decal/down), magnitude, position in time relative to contraction, and shape or duration. To capture these characteristics quantitatively in accordance with an embodiment of the present invention, each heart rate signal is fit with a Gaussian or log-normal distribution function (whichever gives the best fit as ascertained by the sum of squares correlation coefficient, commonly given the symbol $R^2$—only prolonged decels will be best fit with log-normal; all others Gaussian) to yield function parameters. Each data set will be collected as triggered by the onset of a contraction and data collected until the end of a contraction plus 2-3 minutes (to be determined during algorithm optimization).

The Gaussian (eqn. (1)) and log-normal distribution (eqn. (2)) functions are as follows:

$$I = \frac{I_o}{\sqrt{2\pi\sigma^2}} \exp\left(-\frac{(t-t_o)^2}{2\sigma^2}\right) + I_{offset} \quad (1)$$

$$I = \frac{I_o}{t\sigma\sqrt{2\pi}} \exp\left(-\frac{(\ln t - t_o)^2}{2\sigma^2}\right) + I_{offset} \quad (2)$$

Figure 5B:
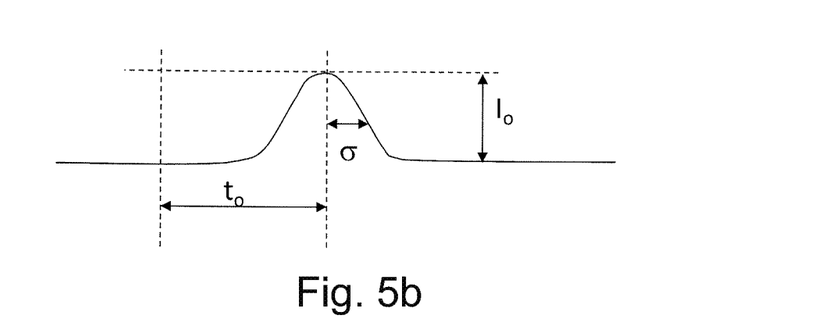

The position, magnitude, and shape/width are parameterized for either the contraction or the fetal heart rate response with $t_o$ (where $M=\ln(t_o)$), $I_o$, and $\sigma$, with $I_{offset}$ being adjusted to the baseline signal. The scheme set forth in FIG. 5b shows this parameterization graphically. With each contraction and associated fetal heart rate response parameterized as shown, fetal health is assessed with an as yet unspecified (to be optimized) functional relationship:

$$\text{Fetal Health} = f(t_{o,c}, I_{o,c}, \sigma_c; t_{o,f}, I_{o,f}, \sigma_f, VAR) \quad (3)$$

where, the "c" and "f" subscripts refer to contraction or fetal heart rate parameters, respectively. In light of the description above concerning subjective assessment, several combinations of the parameters clearly indicate different fetal health conditions and these are now listed.

Accel (okay): Both and $I_{oc}$ and $I_{of}$ are positive quantities and $t_{oc}$ and $t_{of}$ are within several seconds of each other.

Early Decel (okay): $I_{oc}$ and $I_{of}$ are opposite in sign. $I_{of}$ is less than a threshold magnitude of 15 bpm. $t_{oc}$ and $t_{of}$ are within several seconds of each other.

Variable Decel (concern): $I_{oc}$ and $I_{of}$ are opposite in sign. $I_{of}$ is greater than a threshold magnitude of 20-25 bpm. $t_{oc}$ and $t_{of}$ are within several seconds of each other.

Late Decel (significant concern): $I_{oc}$ and $I_{of}$ are opposite in sign. $I_{of}$ is greater than a threshold magnitude of 10 bpm. $t_{of}$ is later than $t_{oc}$ by more than 5 seconds.

Prolonged Decel (significant concern): $I_{oc}$ and $I_{of}$ are opposite in sign. $I_{of}$ is greater than a threshold magnitude of 10 bpm. $t_{of}$ is later than $t_{oc}$ by more than 5 seconds and $\sigma_f$ is larger than 15 seconds. Log-normal is a better fit than the Gaussian function.

All of these above-referenced measures of fetal health will also account for variability (VAR) in the baseline heart rate signal. All of these measures can be indicated on the monitor 65 with appropriate concern levels (green, yellow, or red) indicated with prominence.

Procedurally, the algorithm implementation of an embodiment of the present invention can adopt one or more of the following activities, ultimately embedded in firmware, or in a software program that is implemented by a computer processor, for example: (1) Measure baseline fetal heart rate and variability after most recent contraction; (2) Contraction monitor exceeds a threshold change. This threshold should be determined during patient-specific calibration at the time of initial sensor application and equipment set-up; the threshold should be small enough so that a real contraction triggers data acquisition but large enough so that spurious motion by the patient does not prematurely trigger data acquisition), triggering data acquisition; (3) Upon return of contraction signal to baseline, data is continued to be acquired for the window width (in seconds) times two; (4) Contraction and fetal heart rate data sets are each fit with Gaussian and log-normal distribution functions (Eqns. (1) and (2)) and the one yielding the smallest error is selected for its parameters; and (5) Parameters from the fitting procedure are combined as shown above to objectively assess fetal health.

As will be appreciated by one skilled in the art, aspects of the present invention may be embodied as a system, method or computer program product. Accordingly, aspects of the present invention may take the form of an entirely hardware embodiment, an entirely software embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Figure 6:
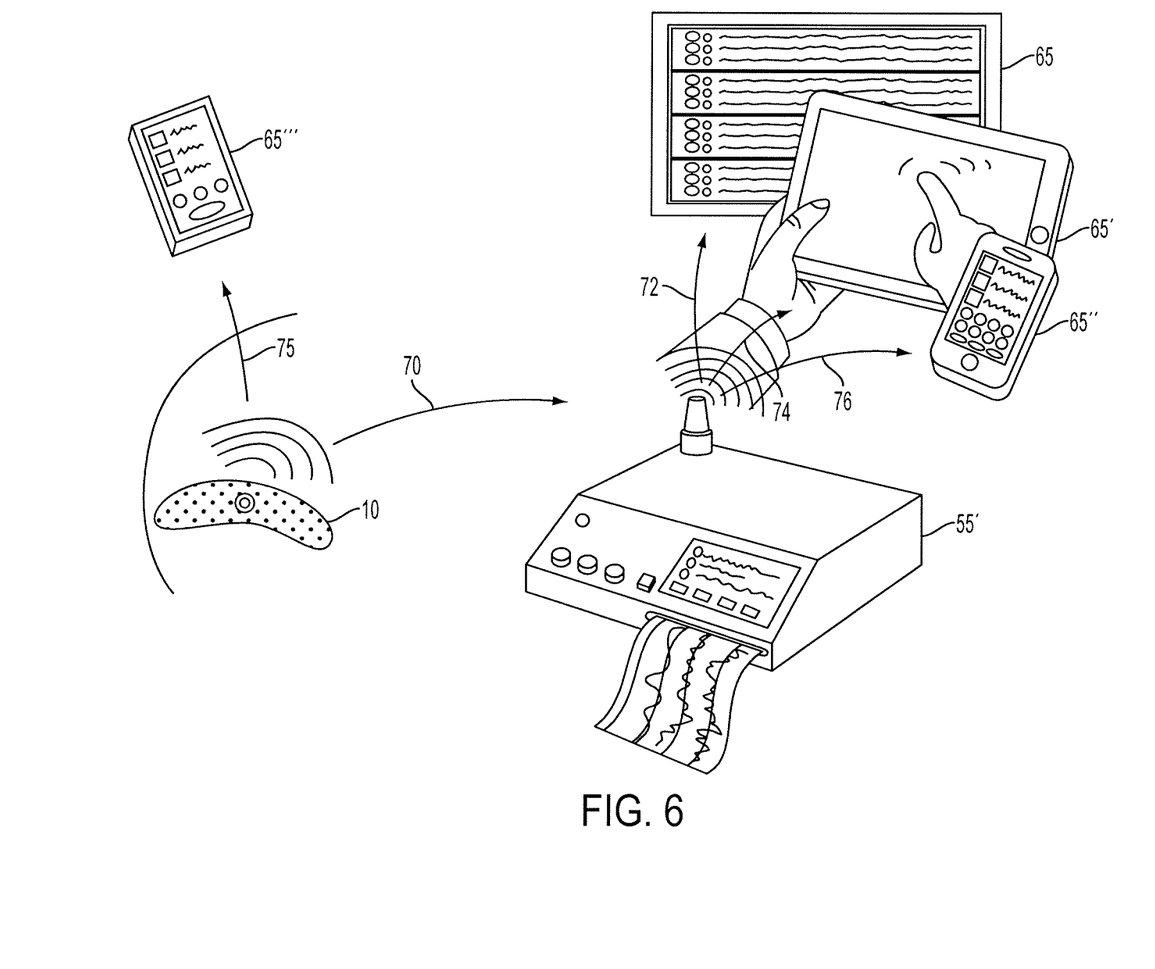
FIG. 6 is a schematic representation of an electronic external fetal monitoring system in accordance with an embodiment of the present invention.

Turning to FIG. 6, another schematic representation of an electronic external fetal monitoring system in accordance with an embodiment of the present invention is shown. patch 10 is shown wirelessly transmitting information (as described above) per arrow 75 to a computer system 65'" (including a smart phone, tablet or other portable computer) in a patient's home, for example. Arrow 75 shows the wireless transmission of the information to a monitor/integrated hardware unit 55' configured to perform the monitoring etc. functionality discussed above and work with the diagnostic algorithms. Arrows 72, 74, and 76 show the wireless transmission of information (as described herein) to a computer system and display screen 65, 65' and 65" (including a smart phone 65''', tablet 65' or other portable computer; and a central nursing station display 65) with a color graphical user interface (e.g., "Red-Yellow-Green").

Figure 7:
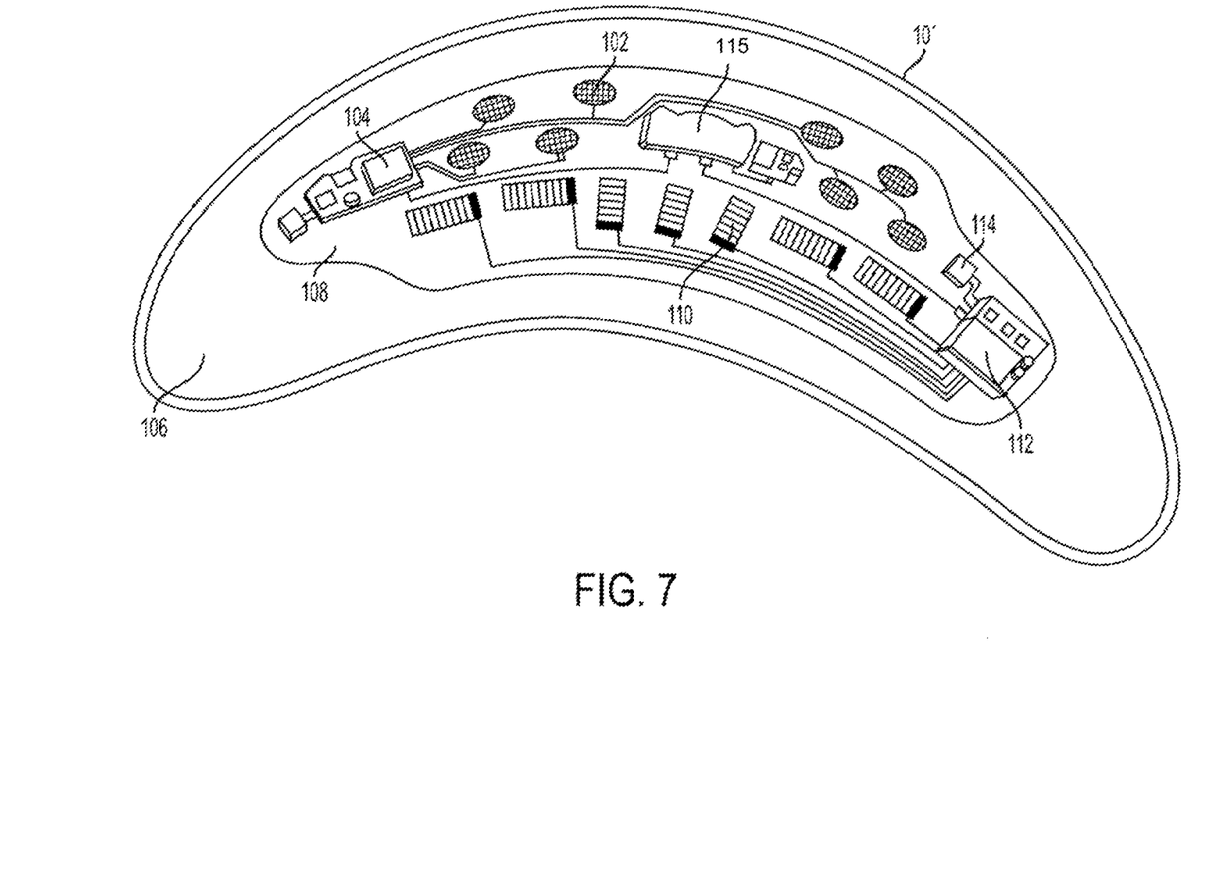
FIG. 7 is a schematic representation of a patch portion of an electronic external fetal monitoring system in accordance with an embodiment of the present invention.

FIG. 7 is a schematic representation of a patch portion 10' of an electronic external fetal monitoring system in accordance with an embodiment of the present invention. Wireless transmitter 115, thin film piezoelectric ultrasound sensor array 102, ultrasound microcontroller 104, patch adhesive 106 (reverse side only) electro-conductive semi-solid gel coating 108 (reverse side only), color-flow Doppler blood leakage sensor array 110, Doppler micro controller 112, and micro batteries 114 are shown.

Figure 8:
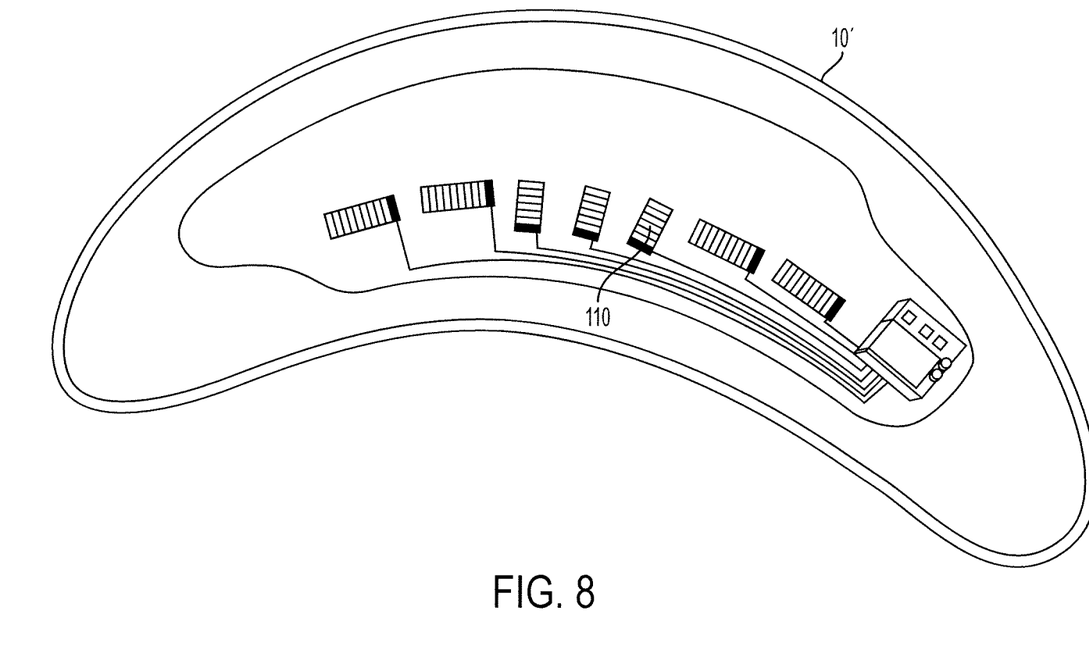
FIG. 8 is a schematic representation of a patch portion of an electronic external fetal monitoring system in accordance with an embodiment of the present invention.

FIG. 8 is a schematic representation of a patch portion 10' of an electronic external fetal monitoring system in accordance with an embodiment of the present invention. Color-flow Doppler blood leakage sensor array 110 is shown, which is configured to (and/or assist with) monitor uterine integrity, migrate existing cardiac Doppler system to uterus, test and validate robustness of data capture and diagnosis of uterine integrity, and finalize interface with partner/existing hardware system(s).

Figure 9:
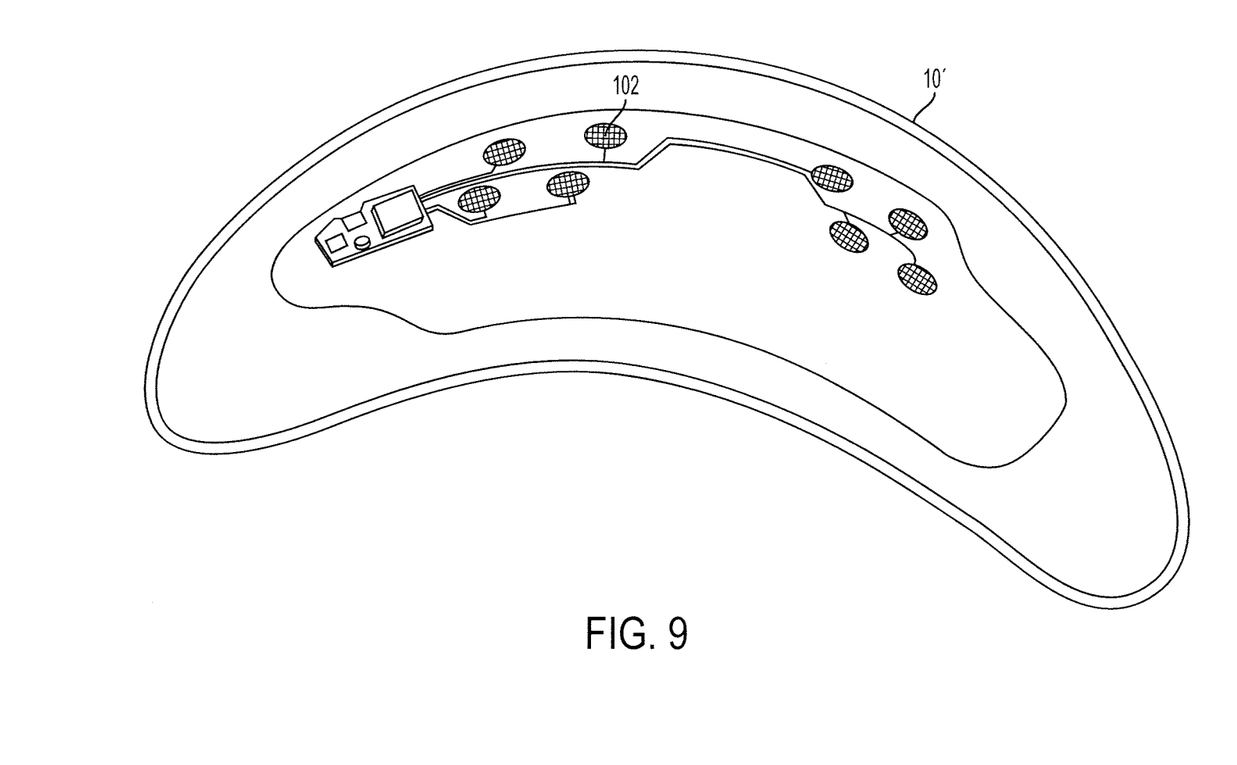
FIG. 9 is a schematic representation of a patch portion of an electronic external fetal monitoring system in accordance with an embodiment of the present invention.

FIG. 9 is a schematic representation of a patch portion 10' of an electronic external fetal monitoring system in accordance with an embodiment of the present invention. Thin film piezo-electric ultrasound sensor array 102, which is configured to (and/or assist with) monitor maternal heart rate, monitor fetal heart rate, monitor uterine contractions, finalize sensor system to find fetal and maternal heart rates, create an algorithm to separate fetal and maternal heart rates, finalize sensors and algorithm to find uterine contractions, test and validate robustness of data capture with placement and movement, finalize interface with partner/existing hardware system(s), and create algorithms to diagnose condition of mother and baby ("red-yellow-green").

Figure 10:
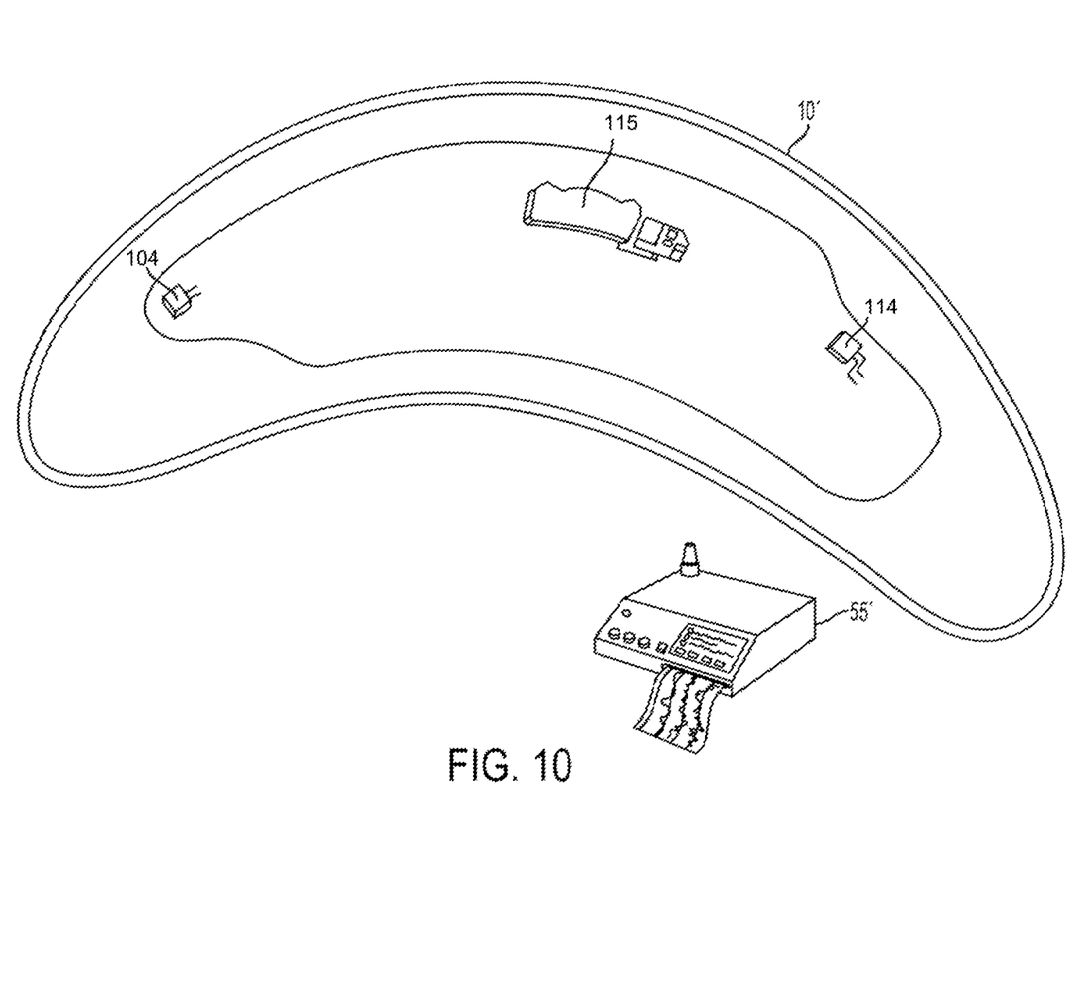
FIG. 10 is a schematic representation of a patch portion of an electronic external fetal monitoring system in accordance with an embodiment of the present invention.

FIG. 10 is a schematic representation of a patch portion 10' of an electronic external fetal monitoring system in accordance with an embodiment of the present invention. Wireless transmitter 100 and a monitor/integrated hardware unit 55' is shown. The wireless transmitter system designated by components 104, 115 and 114 is configured to utilize existing wearable transmitter, battery pack and set-top receiver, develop inexpensive, micro-sized power and transmitter and integrate into disposable strip, and migrate to the monitor/integrated hardware unit 55'.

Other potential uses for the devices contemplated herein include health and wellness monitoring such as patches created for athletes, and military service men. Patches could be created to monitor heartbeat, respiration, pulse oximetry, to track endurance, and surveillance of health. PVDF patches could be made to allow for ultrasound diagnostics in transit in military battlefield applications. Medic on site would apply patch, and data could be viewed at remote treatment facility or hospital while injured is en route.

While several embodiments of the invention have been discussed, it will be appreciated by those skilled in the art that various modifications and variations of the present invention are possible. Such modifications do not depart from the spirit and scope of the present invention.

What is claimed is:

1. An electronic external fetal monitoring system comprising:
   a. a planar dermal patch comprising a first side configured to adhere to the surface of the skin of a pregnant patient, said first side further comprising:
      i. a first portion embedded in said first side and configured to monitor and detect heart rate data;
      ii. a second portion embedded in said first side and configured to monitor and detect uterine activity data; and
      iii. a third portion embedded in said first side and configured to monitor and detect uterine integrity data comprising an acoustic ultrasonic Doppler flow imaging sensor configured to detect blood or amniotic fluid leaking outside the uterine wall, and wherein said uterine integrity data is selected from the group consisting of previous cesarean section integrity data and uterine scarring integrity; and
   b. a computer configured to temporally combine fetal heart rate data acquired from the first portion and uterine activity data acquired from the second portion.

2. The electronic external fetal monitoring system of claim 1, wherein said first side further comprises a self-adhering adhesive material.

3. The electronic external fetal monitoring system of claim 1, wherein at least one of said first portion, said second portion, and said third portion further comprises a layer of acoustic coupling gel.

4. The electronic external fetal monitoring system of claim 1, wherein the heart rate data is selected from fetal heart rate and maternal heart rate.

5. The electronic external fetal monitoring system of claim 4, wherein said first portion is further configured to measure the detected fetal heart rate pursuant to a pitch-catch ultrasound technique.

6. The electronic external fetal monitoring system of claim 4, wherein said first portion is further configured to measure the detected fetal heart rate pursuant to a real-time ultrasound technique.

7. The electronic external fetal monitoring system of claim 1, wherein each of said first portion, said second portion, and said third portion is configured to collect or record at least one selected from the group consisting of the heart rate data, the uterine activity data, and the uterine integrity data.

8. The electronic external fetal monitoring system of claim 7, wherein each of detect, collect, and record the heart rate data, the uterine activity data, and the uterine integrity data, respectively, in real time.

9. The electronic external fetal monitoring system of claim 7, further comprising a fourth portion configured to transmit the heart rate data, the uterine activity data, and the uterine integrity data to a computer device.

10. The electronic external fetal monitoring system of claim 9, wherein the transmission of data is accomplished wirelessly.

11. The electronic external fetal monitoring system of claim 1, wherein said first portion further comprises an ultrasonic transducer comprising a piezoelectric polymer strip.

12. The electronic external fetal monitoring system of claim 11, wherein the second portion comprises a sensor selected from the group consisting of a pressure disc, a strain gauge and a physiologic change sensor.

* * * * *

UNITED STATES PATENT AND TRADEMARK OFFICE
CERTIFICATE OF CORRECTION

PATENT NO.        : 9,820,718 B2
APPLICATION NO.   : 13/782559
DATED             : November 21, 2017
INVENTOR(S)       : Kimberly Flomerfelt et al.

It is certified that error appears in the above-identified patent and that said Letters Patent is hereby corrected as shown below:

Column 14, Claim 8, Line 28, please insert --said first portion, said second portion, and said third portion is configurable to monitor,-- between "of" and "detect"

Signed and Sealed this
Eighth Day of May, 2018

Andrei Iancu
*Director of the United States Patent and Trademark Office*